(12) United States Patent
Yang

(10) Patent No.: US 6,821,733 B2
(45) Date of Patent: Nov. 23, 2004

(54) METHODS AND COMPOSITIONS FOR DETECTING DIFFERENCES BETWEEN NUCLEIC ACIDS

(75) Inventor: Qinghong Yang, Mountain View, CA (US)

(73) Assignee: Panomics, Inc., Redwood City, CA (US)

( * ) Notice: Subject to any disclaimer, the term of this patent is extended or adjusted under 35 U.S.C. 154(b) by 127 days.

(21) Appl. No.: 10/071,299

(22) Filed: Feb. 7, 2002

(65) Prior Publication Data

US 2003/0154033 A1 Aug. 14, 2003

(51) Int. Cl.$^7$ ........................... C12Q 1/68; G01N 33/50
(52) U.S. Cl. ............................................ 435/6; 435/7.1
(58) Field of Search ........................... 435/6, 7.1, 7.91; 702/20

(56) References Cited

U.S. PATENT DOCUMENTS

| | | | |
|---|---|---|---|
| 5,698,400 A | 12/1997 | Cotton et al. ................... | 435/6 |
| 5,824,471 A | 10/1998 | Mashal et al. .................. | 435/6 |
| 6,013,439 A | 1/2000 | Lishanski et al. .............. | 435/6 |
| 6,323,104 B1 * | 5/2001 | Lishanski et al. .......... | 435/91.2 |
| 2002/0042061 A1 * | 4/2002 | Yang et al. ..................... | 435/6 |

FOREIGN PATENT DOCUMENTS

| | | |
|---|---|---|
| WO | WO 97/23646 | 7/1997 |
| WO | WO 00/20643 | 10/1999 |

OTHER PUBLICATIONS

Davies et al., "Formation of RuvABC–Holliday Junction Complexes In Virto" *Current Biology*, 1998, vol. 8 (12), pp 725–727.

Panyutin et al., "Formation of a Single Base Mismatch Impedes Spontaneous DNA Branch Migration" *J. Mol. Biol.*, 1993, vol. 230, pp 413–424.

Saiki et al., "Enzymatic Amplification of β–Globin Genomic Sequences and Restriction Site Analysis for Diagnosis of Sickle Cell Anemia" *Science*, 1985, Dec. 20;230(4732), pp 1350–1354.

Whitby et al., "Interactions Between RuvA and RuvC at Holliday Junctions: Inhibitio of Junction Cleavage and Formation of a RuvA–RuvC–DNA Complex" *J. Mol. Biol.*, 1996, vol. 264, pp 878–890.

PCT International Search Report for PCT/US01/51104, mailed May 13, 2002.

PCT International Search Report for PCT/US01/29922, mailed Feb. 13, 2002.

PCT International Search Report for PCT/US01/07858, mailed Jun. 6, 2001.

Zerbib, D., et al., "Coordinated Actions of RuvABC in Holliday Junction Processing," *J. Mol. Biol.*, (1998) vol. 281, pp. 621–630.

Adams, D., et al., "Unwinding of Closed Circular DNA by the *Escherichia coli* RuvA and RuvB Recombination/Repair Proteins," *J. Mol. Biol.* (1995) vol. 247, pp. 404–417.

Mezard, C., et al., "*Escherichia coli* RuvB$^{L268S}$: a Mutant RuvB Protein That Exhibits Wild–Type Activities In Vitro but Confers a UV–Sensitive ruv Phenotype In Vivo," *Nucleic Acids Research*, (1999) vol. 27, No. 5, pp. 1275–1282.

Panyutin, I., et al., "The Kinetics of Spontaneous DNA Branch Migration," *Proc. Natl. Acad. Sci.*, (1994) vol. 91, pp. 2021–2025 (National Institutes of Health).

* cited by examiner

*Primary Examiner*—Marjorie Moran

(57) ABSTRACT

The present invention provides sensitive methods for detecting the presence or absence of a difference between related nucleic acid sequences. In one aspect of the invention, a method is provided for detecting a difference in the sequence of two nucleic acid molecules. The method includes the steps of: contacting two nucleic acids under conditions that allow the formation of a four-way complex and branch migration; contacting the four-way complex with a tracer molecule and a detection molecule under conditions in which the detection molecule is capable of binding the tracer molecule or the four-way complex; and determining binding of the tracer molecule to the detection molecule before and after exposure to the four-way complex. Competition of the four-way complex with the tracer molecule for binding to the detection molecule indicates a difference between the two nucleic acids. The methods disclosed can be used for detecting nucleotide variations or mutations of an organism, for example, single nucleotide polymorphisms (SNP), which leads to identification of genetic traits associated with diseases or other phenotypic characteristics.

21 Claims, 4 Drawing Sheets

60

90

100

110

METHODS AND COMPOSITIONS FOR DETECTING DIFFERENCES BETWEEN NUCLEIC ACIDS

1. FIELD OF THE INVENTION

Figure 1A:
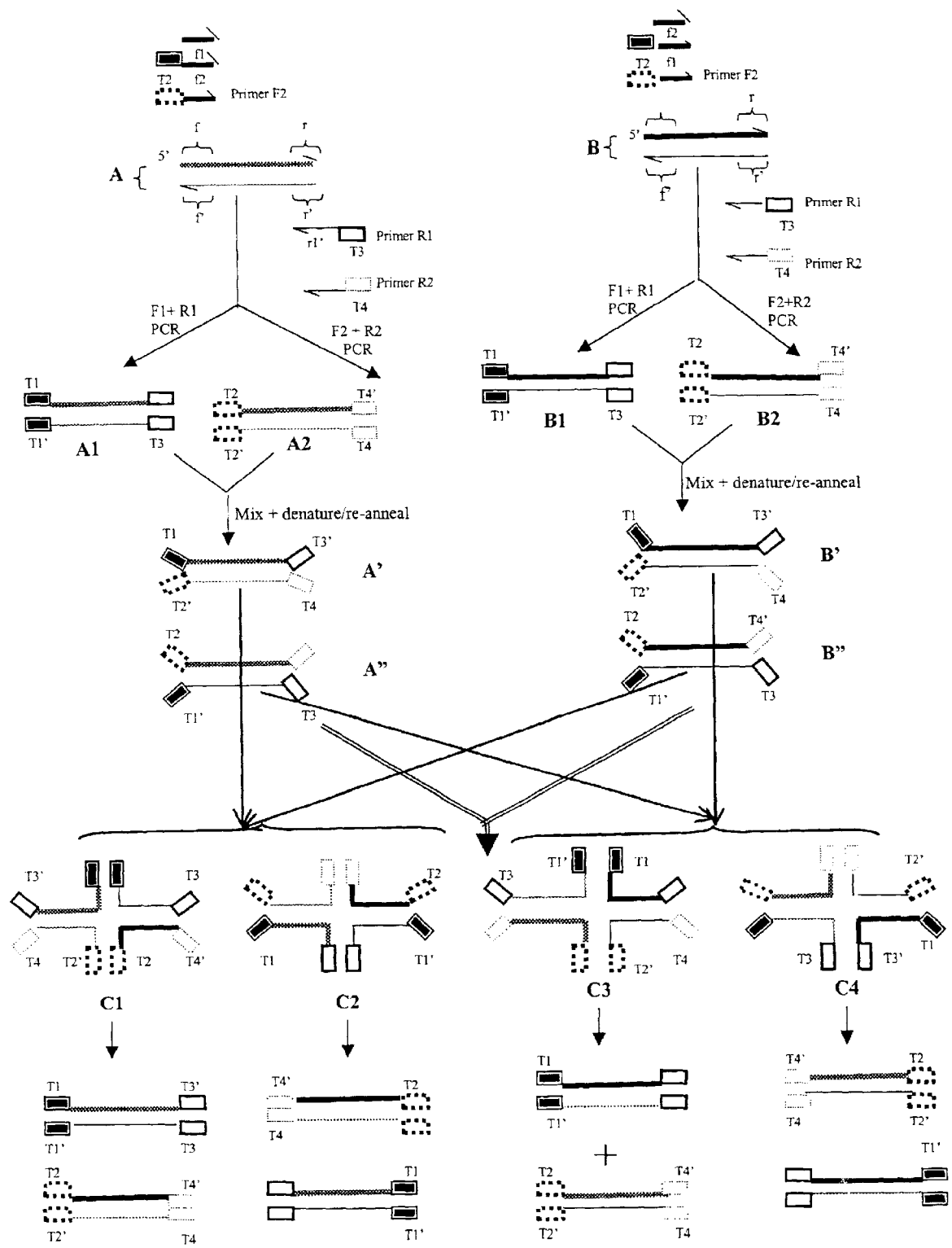

The present invention relates to the fields of molecular biology, chemistry and nucleic acid hybridization. In certain embodiments, the present invention provides methods and compositions that are useful for detecting differences between nucleic acids.

2. BACKGROUND OF THE INVENTION

Breakthroughs in genetics have identified numerous traits that have been associated with diseases. Such traits could be used to accelerate the prevention or treatment of the diseases. For some diseases, a single genetic marker is sufficient to indicate a predisposition for a disease. Detection of the marker can thus indicate an individual at risk for the disease. However, for many diseases, multiple genetic markers interact to generate complex genetic traits that are associated with the diseases. For such diseases, detection of multiple genetic markers might be needed to for the treatment or prevention of the disease. Methods of rapidly and accurately detecting such genetic markers are needed to improve the treatment or prevention of diseases that can be associated with genetic markers.

Many such genetic markers are single-nucleotide polymorphisms (SNPs). Such SNPs are distributed throughout the genome at frequency of about 1 per 1,000 base pairs. Several hundred thousand of these markers are now available in public databases. These databases should facilitate the identification of genetic markers associated with simple and complex diseases. However, efficient methods to rapidly identify and/or detect SNPs are needed to utilize such genetic markers for effective treatment or prevention of the diseases.

Conventional methods have been used for the detection of SNPs and other genetic markers. Traditional methods include direct sequencing of polynucleotides and direct measurement of restriction fragment length polymorphisms. In addition, methods based on the hybridization of probes to genetic markers have been used. Such methods include oligonucleotide chips, polymerase chain reaction amplification of genetic markers and other such techniques.

However, such conventional techniques often suffer from poor accuracy, high cost or low throughput. For example, current hybridization-based genotyping methods such as SNP-chip or micro-array often lack sufficient sensitivity and/or accuracy to detect many SNPs simultaneously with a uniform set of conditions. A polynucleotide comprising one version of an SNP is often capable of hybridizing to a polynucleotide comprising a second version of the same SNP when assayed according to conventional techniques. Although hybridization is stronger between two perfectly complementary polynucleotides, single base-pair differences are often not sufficient to detect many SNPs simultaneously with the same set of conditions required for SNP-chip or micro-array.

The need thus remains for a less costly, more accurate method to detect the presence or absence of sequence differences between polynucleotide samples, for example, at many different SNP positions with very high throughput.

3. SUMMARY OF THE INVENTION

Accordingly, the present invention provides methods for detecting the presence or absence of a difference between two related nucleic acid sequences. The methods achieve sensitivities great enough to detect the presence of any difference between the nucleic acids, even single nucleotide polymorphisms.

In one aspect, the present invention provides methods of detecting a difference between two nucleic acids. In the methods, the nucleic acids are contacted under conditions in which they are capable of forming a four-way complex. A four-way complex is a macromolecular structure that comprises both nucleic acids in double stranded form. Typically, a four-way complex comprises a Holliday junction. A Holliday junction is known to those of skill in the art as the branch point in a complex of two related (often identical) double stranded nucleic acids. If the nucleic acids share identical sequences and the sequence identity extends to the ends of the nucleic acids, the four-way complex is capable of undergoing branch migration under the appropriate conditions resulting in resolution into two double stranded sequences. Significantly, if sequence identity and complementarity does not extend to the ends of the nucleic acids, migration of the four-way complex can halt at or near a site where the sequences are not identical or complementary.

The conditions under which the nucleic acids are contacted are chosen so that the four-way complex is capable of allele-specific four-way complex migration. Such conditions are known to those of skill in the art and include those under which migration of a four-way complex can proceed along the strands of the nucleic acids that comprise identical or complementary sequences. Typically, conditions are chosen such that migration will proceed to completion only if the two nucleic acids are identical in sequence. Thus, if there is no difference between the nucleic acids, migration can proceed to completion thereby resolving the four-way complex to yield two double stranded nucleic acid products. If there is a difference in sequence between the two nucleic acids, one or more base mismatches can form that can be capable of impeding four-way complex migration resulting in a stabilized four-way complex if the mismatches pose a sufficient energy barrier to migration. Detection of the stabilized four-way complex indicates a difference between the sequences of the nucleic acids.

In certain embodiments of the invention, mutations can be introduced into one or both nucleic acids to promote allele-specific four-way complex migration. Such mutations are typically near the site of a polymorphism and do not impede four-way complex migration unless the nucleic acids differ at the site of the polymorphism. Such mutations are described in detail in copending U.S. application Ser. No. 10/071,302, the contents of which are hereby incorporated by reference in their entirety.

In order to detect any stabilized four-way complexes, the nucleic acids are contacted with a detection molecule in a solution comprising a tracer molecule or tracer molecules. The detection molecule can be any molecule that is capable of selectively binding a four-way complex of nucleic acids such as a Holliday junction. Suitable detection molecules are known to those of skill in the art and include, but are not limited to RuvA, RuvC, RuvB, RusA, RuvG, and mutants, analogs or fragments thereof. Binding of the detection molecule by a stable four-way complex of the nucleic acids indicates a difference between the nucleic acids. This binding can be detected with the tracer molecules.

The tracer molecule can be used to detect the binding of the detection molecule to the stable four-way complex of the nucleic acids. The tracer molecule can be any molecule capable of selectively binding the detection molecule. When co-existing in solution, the tracer molecule can compete with the four-way complex for binding to the detection molecule. Preferably, the tracer molecule comprises one or more oligonucleotides that are capable of forming a stable or immobile four-way complex. Significantly, the tracer molecule also comprises a detectable label. The detectable label should be capable of generating a detectable signal that is sensitive to binding of the tracer molecule by the detection molecule. In other words, the detectable signal upon binding by the detection molecule should be distinguishable from the detectable signal in the absence of binding by the detection molecule. The detectable signal can be detected by methods known to those of skill in the art for detecting the signal.

Binding of the four-way complex of nucleic acids by the detection molecule is indicated by detecting the extent of the binding of the tracer molecule by the detection molecule. If the four-way complex of nucleic acids is stable, the four-way complex should compete with the tracer molecule for binding by the detection molecule. As such, the level of the detectable signal generated upon binding of the tracer molecule to the detection molecule will be determined by the existence/quantity of the co-existing competitive stable four-way complex. As a result, the level of the detectable signal indicates a stable four-way complex and thus the existence or absence of a difference between the nucleic acids.

The methods and compositions of the invention can be used in any application for which the detection of differences between nucleic acids is useful. Such applications include genotyping, SNP identification, SNP scoring, nucleic acid sequencing, and so forth. The methods and compositions of the invention provide sensitive and efficient methods of detecting any difference between two nucleic acids. Moreover, the methods and compositions of the invention can also be used for the detection/quantification of any nucleic acids of interest, including both DNA and RNA.

4. BRIEF DESCRIPTION OF THE FIGURES

Figure 1B:
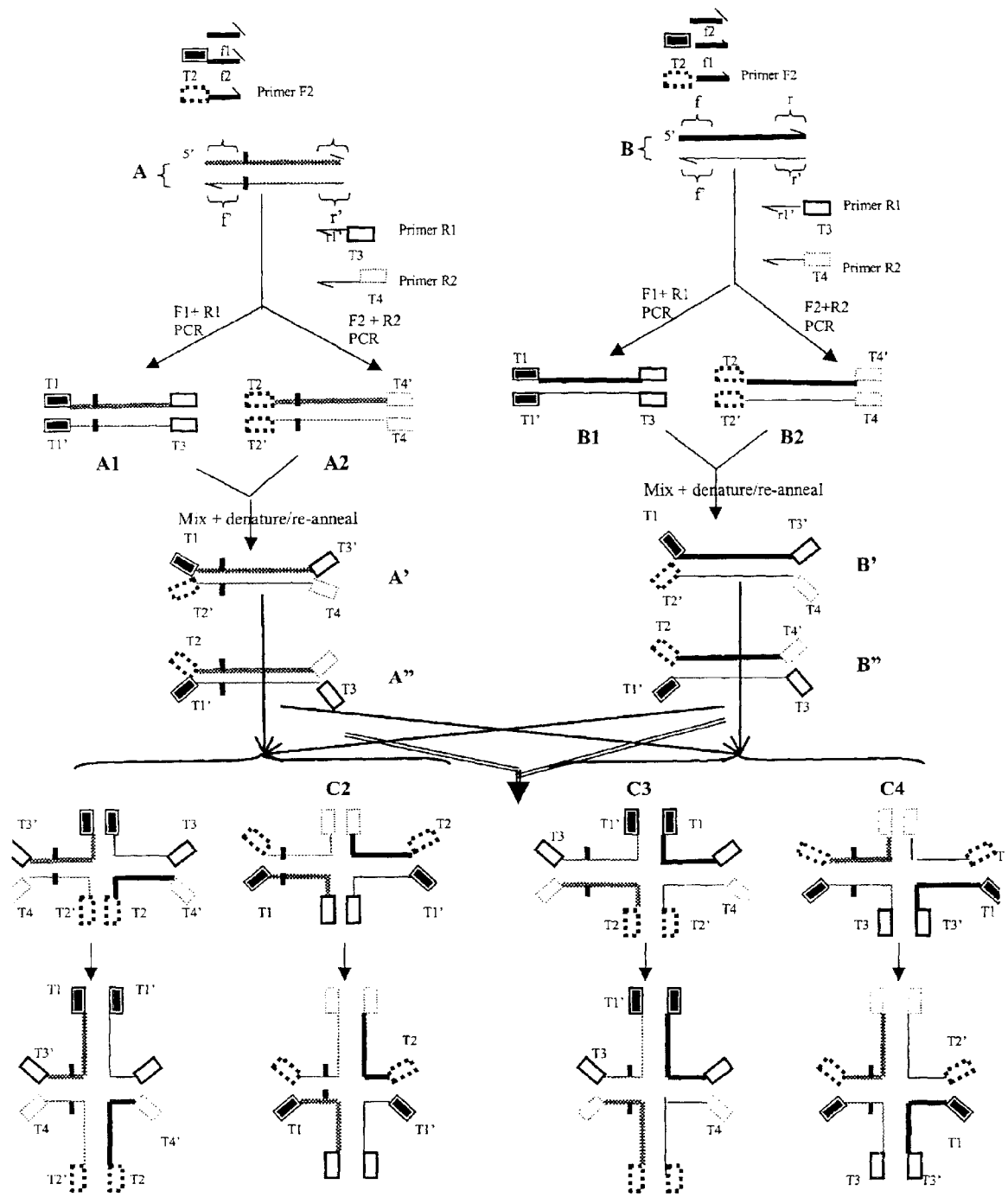
Figure 2:
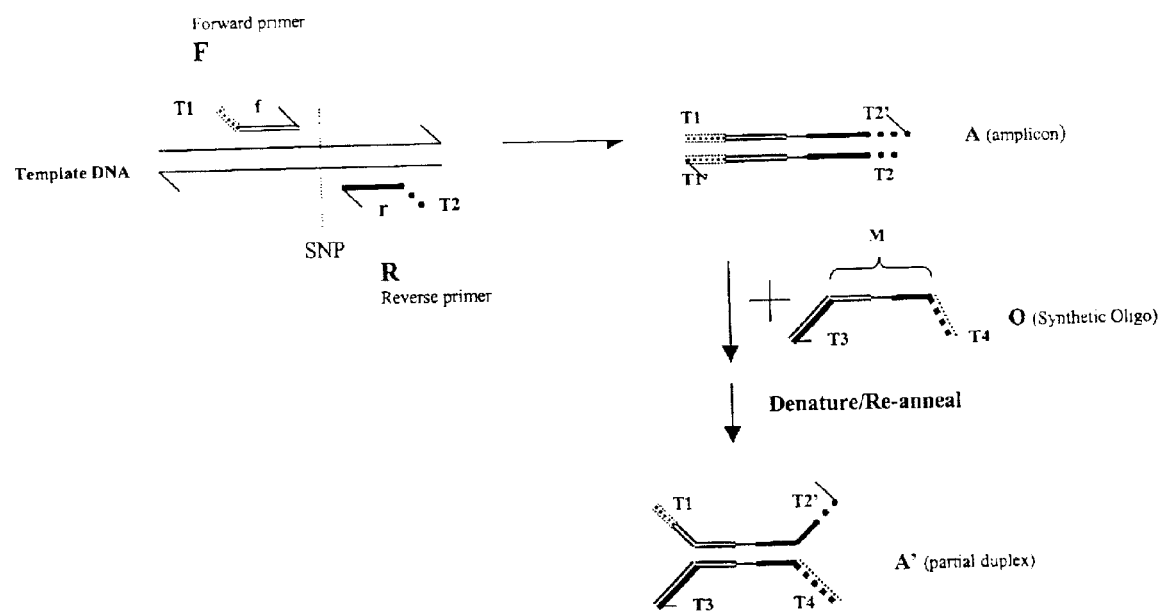
Figure 3:
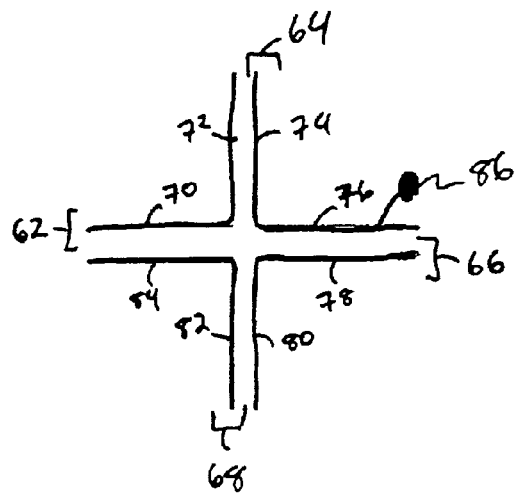
Figure 3:
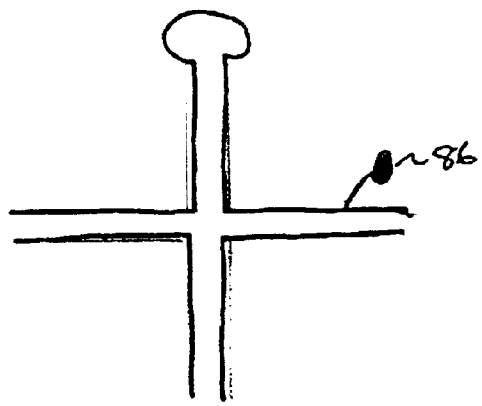
Figure 3:
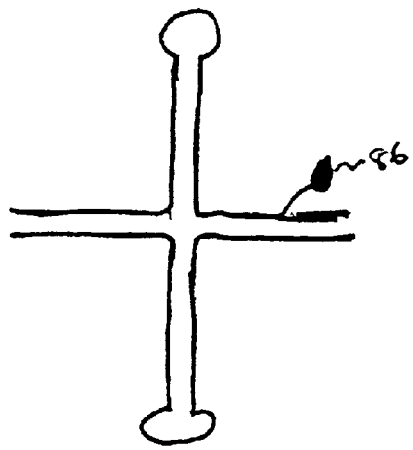
Figure 3:
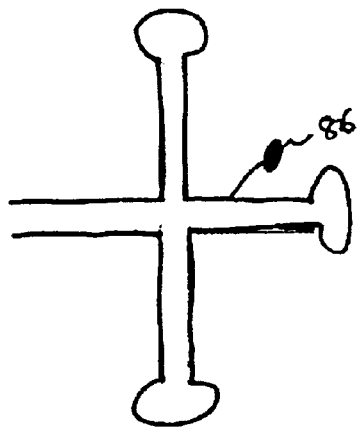

FIG. 1A and FIG. 1B provide an illustration of the preparation of a typical partial duplex of nucleic acid by PCR and formation of four-way complexes C1, C2, C3, and C4, which are then subject to branch migration conditions; FIG. 1A illustrates that if there is no mismatch between sequences A and B, each of the four complexes C1, C2, C3, and C4 resolves into duplexes; and FIG. 1B illustrates that if there is a mismatch or mismatches between sequences A and B, each of the four complexes C1, C2, C3, and C4 forms a stabilized four-way complex;

FIG. 2 provides an illustration of the preparation a typical partial duplex of nucleic acids by hybridization of a PCR product and a synthetic partially complementary oligonucleotide; and FIG. 3 provides illustrations of tracer molecules.

5. DETAILED DESCRIPTION OF THE PREFERRED EMBODIMENTS 5.1 Abbreviations

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Also, unless specified otherwise, nucleic acid sequences that are represented as a series of one-letter abbreviations are presented in the 5'->3' direction.

5.2 Definitions

As used herein, the terms "nucleic acid" and "polynucleotide" are interchangeable and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

The terms nucleic acid, polynucleotide, and nucleotide also specifically include nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, and 2,6-diaminopurine.

Furthermore, a polynucleotide of the invention may comprise at least one modified sugar moiety selected from the group including but not limited to arabinose, 2-fluoroarabinose, xylulose, and hexose. It is not intended that the present invention be limited by the source of the polynucleotide. The polynucleotide can be from a human or non-human mammal, or any other organism, or derived from any recombinant source, synthesized in vitro or by chemical synthesis. The polynucleotide may be DNA, RNA, cDNA, DNA-RNA, peptide nucleic acid (PNA), a hybrid or any mixture of the same, and may exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

The nucleic acid can be only a minor fraction of a complex mixture such as a biological sample. The nucleic acid can be obtained from a biological sample by procedures well known in the art.

A polynucleotide of the present invention can be derivitized or modified, for example, for the purpose of detection, by biotinylation, amine modifictaion, alkylation, or other like modification. In some circumstances, for example where increased nuclease stability is desired, the invention can employ nucleic acids having modified internucleoside linkages. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide, dimethylenesulfoxide, dimethylene-sulfone, 2'-O-alkyl, and 2'-deoxy-2'-fluoro phosphorothioate internucleoside linkages are well known in the art (see Uhlman et al., 1990, *Chem. Rev.* 90:543–584; Schneider et al. 1990, *Tetrahedron Lett*. 31:335, and references cited therein).

The term "oligonucleotide" refers to a relatively short, single stranded polynucleotide, usually of synthetic origin. An oligonucleotide typically comprises a sequence that is 8 to 100 nucleotides, preferably, 20 to 80 nucleotides, and more preferably, 30 to 60 nucleotides in length. Various techniques can be employed for preparing an oligonucleotide utilized in the present invention. Such an oligonucleotide can be obtained by biological synthesis or by chemical synthesis. For short sequences (up to about 100 nucleotides) chemical synthesis will frequently be more economical compared to biological synthesis. In addition to economy, chemical synthesis provides a convenient way of incorporating low molecular weight compounds and/or modified bases during synthesis. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing, 1983, *Methods Enzymol.* 101:20–78. Other methods of oligonucleotide synthesis include phosphotriester and phosphodiester methods (Narang et al., 1979, *Meth. Enzymol.* 68:90) and synthesis on a support (Beaucage et al., 1981, *Tetrahedron Letters* 22:1859–1862) as well as phosphoramidate synthesis, Caruthers et al., 1988, *Meth. Enzymol.* 154:287–314, and others described in "Synthesis and Applications of DNA and RNA," S. A. Narang, editor, Academic Press, New York, 1987, and the references contained therein.

An oligonucleotide "primer" can be employed in a chain extension reaction with a polynucleotide template such as in, for example, the amplification of a nucleic acid. The oligonucleotide primer is usually a synthetic oligonucleotide that is single stranded, containing a hybridizable sequence at or near its 3'-end that is capable of hybridizing with a defined sequence of the target or reference polynucleotide. Normally, the hybridizable sequence of the oligonucleotide primer has at least 90%, preferably 95%, most preferably 100%, complementarity to a defined sequence or primer binding site. In certain embodiments of the invention, the sequence of a primer can vary from ideal complementarity to introduce mutations into resulting amplicons, as discussed below. The number of nucleotides in the hybridizable sequence of an oligonucleotide primer should be such that stringency conditions used to hybridize the oligonucleotide primer will prevent excessive random non-specific hybridization. Usually, the number of nucleotides in the hybridizable sequence of the oligonucleotide primer will be at least ten nucleotides, preferably at least 15 nucleotides and, preferably 20 to 50, nucleotides. In addition, the primer may have a sequence at its 5'-end that does not hybridize to the target or reference polynucleotides that can have 1 to 60 nucleotides, 5 to 30 nucleotides or, preferably, 8 to 30 nucleotides.

The term "sample" refers to a material suspected of containing a nucleic acid of interest. Such samples include biological fluids such as blood, serum, plasma, sputum, lymphatic fluid, semen, vaginal mucus, feces, urine, spinal fluid, and the like; biological tissue such as hair and skin; and so forth. Other samples include cell cultures and the like, plants, food, forensic samples such as paper, fabrics and scrapings, water, sewage, medicinals, etc. When necessary, the sample may be pretreated with reagents to liquefy the sample and/or release the nucleic acids from binding substances. Such pretreatments are well known in the art.

The term "amplification," as applied to nucleic acids refers to any method that results in the formation of one or more copies of a nucleic acid, where preferably the amplification is exponential. One such method for enzymatic amplification of specific sequences of DNA is known as the polymerase chain reaction (PCR), as described by Saiki et al., 1986, *Science* 230:1350–1354. Primers used in PCR can vary in length from about 10 to 50 or more nucleotides, and are typically selected to be at least about 15 nucleotides to ensure sufficient specificity. The double stranded fragment that is produced is called an "amplicon" and may vary in length form as few as about 30 nucleotides to 20,000 or more. The term "chain extension" refers to the extension of a 3'-end of a polynucleotide by the addition of nucleotides or bases. Chain extension relevant to the present invention is generally template dependent, that is, the appended nucleotides are determined by the sequence of a template nucleic acid to which the extending chain is hybridized. The chain extension product sequence that is produced is complementary to the template sequence. Usually, chain extension is enzyme catalyzed, preferably, in the present invention, by a thermostable DNA polymerase, such as the enzymes derived from *Thermis acquaticus* (the Taq polymerase), *Thermococcus litoralis*, and *Pyrococcus furiosis*.

A "Holliday junction" is the branch point in a four-way junction in a complex of two related (often identical) nucleic acid sequences and their complementary sequences. The junction is capable of undergoing branch migration resulting in dissociation into two double stranded sequences where sequence identity and complementarity extend to the ends of the strands. Holliday junctions, their formation and branch migration are concepts familiar to those of skill in the art, and are described, for example, by Whitby et al., 1996, *J. Mol. Biol*. 264:878–890, and Davies & West, 1998, *Current Biology* 8:727–727.

"Branch migration conditions" are conditions under which migration of a four-way complex can proceed along the component polynucleotide strands. Normally in the practice of the invention, conditions are chosen such that migration will proceed only if strand exchange does not result in an increase in the number of mismatches in the complementary regions of the four-way complex, wherein a net increase in the number of base mismatches can impede branch migration, resulting in a stabilized four-way complex. Appropriate conditions can be found, for example, in Panyutin and Hsieh, 1993, *J. Mol. Biol*. 230:413–424. In certain applications the conditions will have to be modified due to the nature of the particular polynucleotides involved. Such modifications are readily discernible by one of skill in the art without undue experimentation.

A "stabilized" four-way complex is a junction where a mismatch has stalled branch migration to an extent sufficient that the stabilized four-way complex is detectable and distinguishable from the duplex DNA that would be released from a four-way complex involving identical sequences owing to branch migration.

Two nucleic acid sequences are "related" or "correspond" when they are either (1) identical to each other, or (2) would be identical were it not for some difference in sequence that distinguishes the two nucleic acid sequences from each other. The difference can be a substitution, deletion or insertion of any single nucleotide or a series of nucleotides within a sequence. Such difference is referred to herein as the "difference between two related nucleic acid sequences." Frequently, related nucleic acid sequences differ from each other by a single nucleotide. Related nucleic acid sequences typically contain at least 15 identical nucleotides at each end but have different lengths or have intervening sequences that differ by at least one nucleotide.

The term "mutation" refers to a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions and frame-shift mutations. The latter entail the insertion or deletion of one to several nucleotide pairs. A difference of one nucleotide can be significant as to phenotypic normality or abnormality as in the case of, for example, sickle cell anemia.

A "duplex" is a double stranded nucleic acid sequence comprising two complementary sequences annealed to one another. A "partial duplex" is a double stranded nucleic acid sequence wherein a section of one of the strands is complementary to the other strand and can anneal to form a partial duplex, but the full lengths of the strands are not complementary, resulting in a single-stranded polynucleotide tail at at least one end of the partial duplex.

The terms "hybridization," "binding" and "annealing," in the context of polynucleotide sequences, are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is typically achieved by elevating the temperature, increasing the ratio of cosolvents, lowering the salt concentration, and other such methods well known in the field.

Two sequences are "complementary" when the sequence of one can bind to the sequence of the other in an antiparallel sense wherein the 3'-end of each sequence binds to the 5'-end of the other sequence and each A, T(U), G, and C of one sequence is then aligned with a T(U), A, C, and G, respectively, of the other sequence.

A "detection molecule" is any molecule that is capable of selectively binding a four-way complex of nucleic acids such as a Holliday junction. Suitable detection molecules are known to those of skill in the art and include, but are not limited to RuvA, RuvC, RuvB, RusA, RuvG, and mutants, analogs or fragments thereof "Mutants" of detection molecules include detection molecules comprising mutations that retain their capability of selectively binding a four-way complex of nucleic acids. Examples of such mutants are described below. "Analogs" of detection molecules include, for example, analogs of RuvA, RuvC, RuvB, RusA and RuvG isolated from species other than *E. coli*. Preferred analogs include thermostable analogs.

A "tracer molecule" is any molecule capable of selectively binding the detection molecule. When co-existing in solution, the tracer molecule can compete with the four-way complex for binding to the detection molecule. Preferably, the tracer molecule comprises one or more oligonucleotides that are capable of forming a stable or immobile four-way complex and a detectable label.

5.3 Methods of Detecting a Difference between Nucleic Acids

The present invention is universal and permits detection of a difference in two related nucleic acid sequences, regardless of whether such difference is known a priori. Such differences include any mutation within a nucleic acid sequence, e.g., a single or multiple base substitution or polymorphism, a deletion or an insertion. Methods of the invention are rapid, convenient, and amenable to automation, and can be conducted in a homogeneous or heterogeneous format. They are ideally suited for rapid mutation pre-screening and genotyping, particularly involving the identification of single nucleotide polymorphisms (SNPs). The disclosed methods are sensitive and quantitative, and are particularly amenable to application with polymerase chain reaction (PCR).

In general, the present invention provides methods and compositions useful for the detection of a difference between two related nucleic acid sequences by determining whether constructs comprising the sequences are capable of forming a stabilized four-way complex. Accordingly, the present invention provides methods and compositions useful for detecting such four-way complexes. For instance, in one exemplary embodiment of the invention, the stabilized four-way complex junction is detected by means of one or more detection molecules capable of specifically binding a four-way complex. Specific embodiments of the invention are disclosed herein to illustrate the invention and to enable one skilled in the art to practice the invention. The specific embodiments are not intended to limit the scope of the invention.

5.3.1 The Nucleic Acids

The invention provides methods and compositions for detecting a difference between two polynucleotide sequences by means of the formation of a stabilized four-way complex involving polynucleotide constructs comprising the sequences, as illustrated in FIG. 1. For purposes of describing the invention, it will be convenient to refer to the two sequences being compared as a target sequence and a reference sequence. The reference sequence is typically a polynucleotide of substantially known sequence, and the target sequence is a related sequence for which it is desired to detect the presence or absence of a difference relative to the reference sequences. However, the invention is useful for detecting a difference between any two polynucleotide sequence. Of the two polynucleotide sequences, either can be a reference sequence, and the other can be a target sequence.

Preferably, the two polynucleotide sequences are related or correspond. The sequences can be related if the sequences are either identical, or would be identical if not for some difference between the two sequences. In preferred embodiments of the invention, the difference is a substitution, deletion or insertion variation or mutation, such as but not limited to a single nucleotide polymorphism (SNP). In some embodiments of the invention, discussed below, one or more extra mutations, in addition to the difference, can be introduced into one or both polynucleotide sequences to improve the accuracy of the method.

According to the methods of the present invention, the target sequence is typically prepared as a pair of sequences wherein each sequence of the pair is capable of forming a partial duplex. Similarly, the reference sequence is also typically prepared as a pair of sequences wherein each sequence of the pair is capable of forming a partial duplex. Partial duplexes prepared from the target sequence and reference sequence should be capable of forming a four-way complex when contacted under the appropriate conditions.

The target polynucleotide sequence can be of any length so long as the reference partial duplex, together with the reference partial duplex, is capable of allele-specific four-way complex migration. Significantly, the methods of the present invention allow allele-specific four-way complex migration even when the target polynucleotide sequence is less than 100 base pairs in length. In preferred embodiments of the invention, the target polynucleotide sequence is at least 8 base pairs, 10 base pairs, 20 base pairs, 30 base pairs, 40 base pairs in length. The target polynucleotide sequence can be as long as desired. Preferably, the target polynucleotide sequence is not so long that the target polynucleotide sequence comprises the sites of more than one polymorphism.

The reference polynucleotide sequence can be of any length so long as the reference partial duplex, together with the target partial duplex, is capable of allele-specific four-way complex migration. Significantly, the methods of the present invention allow allele-specific four-way complex migration even when the reference polynucleotide sequence is less than 100 base pairs in length. In preferred embodiments of the invention, the reference polynucleotide sequence is at least 8 base pairs, 10 base pairs, 20 base pairs, 30 base pairs, 40 base pairs in length. The reference polynucleotide sequence can be as long as desired. Preferably, the reference polynucleotide sequence is not so long that the reference polynucleotide sequence comprises the sites of more than one polymorphism.

Partial duplexes are described in detail in U.S. Pat. No. 6,013,439, in U.S. Pat. No. 6,232,104 B1 and in PCT publication WO 01/69200, each of which is hereby incorporated by reference in its entirety. A typical partial duplex A' is illustrated in FIG. 1. Partial duplex A' comprises a complementary duplex region and one or more tail regions. A complementary duplex region comprises a target sequence or a reference sequence annealed to its complement. Other examples of partial duplexes are illustrated as A", B' and B".

In partial duplex A', one tailed region comprises the oligonucleotide tails T1 and T2'. Similarly, a second tailed region comprises the oligonucleotide tails T3' and T4. Tail T1', T2', T3' and T4' are the complementary strands of tail T1, T2, T3, T4, respectively. Tail T1, T2, T3, T4, T1', T2', T3' and/or T4' can be linked to the target sequence via any linkage known to those of skill in the art for linking polynucleotides. They can be linked directly via a covalent bond or via a linker. The linker can be a polynucleotide or any other linker known to those of skill in the art. Preferably, tail T1, T2, T3, T4, T1', T2', T3' and/or T4' can be linked to a target sequence or a reference sequence via a phosphodiester linkage.

In some embodiments of the invention, a partial duplex has one tail region. In other embodiments of the invention, a partial duplex has two tail regions. Tails T1, T2, T3, T2', T3' and T4 are preferably 0 bp–500 bp and more preferably 0 bp–55 bp as long as one pair of tails at one terminus of the partial duplexes are longer than 10 bp.

All four tails are comprised of sequences that are unrelated to each other. In some preferred embodiments, all 4 tails are not related to the template DNA. In other preferred embodiments, one of the pair of polynucleotide tails at each terminus of the partial duplexes (e.g.: T1/T2' or T3'/T4 partial duplex A' in FIG. 1) can be template DNA sequences. Preferably, a tail is capable of hybridizing with another sequence that complements the tail without interference from the target sequence, the reference sequence or from other tails.

So that they are capable of forming a four-way structure, two or more partial duplexes can be prepared with the same target sequence and a corresponding reference sequence. For instance, partial duplexes A' and B", illustrated in FIG. 1, are capable of forming a four-way structure under the appropriate conditions. In FIG. 1, partial duplex A' comprises the tails T1, T2', T3', and T4. Another partial duplex B" comprises the tails T1', T2, T3 and T4'. Each pair of polynucleotide tails at each end of the partial duplexes, e.g., T1/T2', T2/T1', T3'/T4, T3/T4' are not complementary and will not anneal to one another under the applicable conditions. However, tail T3' at the right end of partial duplex A' is complementary to, and hence can hybridize with, tail T3 at the right end of partial duplex B". Tail T4 at the right end of partial duplex A' is complementary to, and hence can hybridize with, tail T4' at the right end of partial duplex B". Tail T1 at the left end of partial duplex A' is complementary to, and hence can hybridize with, tail T1" at the left end of partial duplex B". Tail T2' at the left end of partial duplex A' is complementary to, and hence can hybridize with, tail T2 at the left end of partial duplex B".

5.3.2 Preparation of Nucleic Acids

The partial duplexes described above can be prepared by any method known to those of skill in the art for the preparation of polynucleotides or nucleic acids. For instance, the partial duplexes can be prepared by standard recombinant, synthetic or PCR techniques, or a combination thereof. In addition, the partial duplexes, or portions thereof such as the target or reference sequence, can be isolated from natural sources. The simplest way to make partial duplexes is by annealing two synthetic oligos that are partially complementary to each other. Exemplary PCR methods of preparing sequences that are capable of forming partial duplexes are described in U.S. Pat. No. 6,013,439, in U.S. Pat. No. 6,232,104 B1 and in PCT publication WO 01/69200, each of which is hereby incorporated by reference in its entirety.

For example, partial duplexes can be prepared by the following PCR techniques. FIG. 1 illustrates the preparation of partial duplexes A', A", B' and B" by a PCR technique. To prepare the partial duplexes, nucleic acids A and B can be amplified, either separately or jointly, by standard PCR using a common set of primers made up of one or more forward primers and two reverse primers R1 & R2. R1 and R2 can either share the same 3' end (r'=r1'=r2') that hybridizes to the same part of template DNA or the 3' end of R1 and R2 can hybridize to different parts of the template DNA (r1'≠r2'). As illustrated in FIG. 1, forward primer F1 or forward primer F2 can be used in the PCR reaction. If forward primer F1 is used, duplexes with T1/T1' tails will be generated such as A1. If forward primer F2 is used, duplexes with T2/T2' tails will be generated such as A2. Two forward primers can also be used to generate partial duplexes at the end corresponding to the forward primer. For instance, using forward primers F1 and F2 in the same PCR reaction generates sequences that can be used to produce partial duplexes A' and A". In addition, a forward primer with no tails (two of the 4 tails are 0 bp) can be used to generate a duplex with no tails at the end corresponding to the forward primer.

The entire sequence of the forward primer F hybridizes with the template DNA, i.e., both A and B. Forward primers F1 and F2 can share their 3' end (f1=f2) and hybridize with the same part of template DNA (reference and target DNA), or alternatively, primer F1 and F2 can have different 3' ends and therefore hybridize with different parts of template DNA (f1≠f2). In addition, F1 has a 5'-end portion (T1) that does or does not hybridize with the template DNA. Likewise, F2 has a 5'-end portion (T2) that does or does not hybridize with the template DNA. The two reverse primers R1 and R2 can share a common 3'-end portion (r'=r1'=r2') that hybridizes with the same part of template DNA, or alternatively, primer R1 and R2 can have different 3' end and therefore hybridize with different part of template DNA. In addition, R1 has a 5'-end portion (T3) that does not hybridize with the template DNA. Likewise, R2 has a 5'-end portion (T4) that is not complementary to and hence does not hybridize with the template DNA. T3 is not related with T4, i.e., the complementary strand of T3 (T3') is not complementary to T4 and the complementary strand of T4 (T4') is not complementary to T3. As a result, T4' will not hybridize with T3 under the conditions employed in the method. Multiple rounds of PCR amplification will result in the formation of a number of DNA products, including the component strands of the four tailed partial duplexes A', A", B', B" (FIG. 1). The tailed duplexes are formed by adjusting the temperature of the solution so that the component strands can hybridize to form the desired partial duplexes. Note that a number of other duplexes will also be formed. These unintended products generally do not pose a problem because a sufficient number of partial duplexes are formed under the conditions described above.

Each tailed partial duplex A' is comprised of a duplex of two complementary nucleic acid strands of duplex A and, at one end of the duplex, two non-complementary oligonucleotide tails T3' and T4. Depending on the choice of forwarding primer, partial duplex A' can have either zero, one or two tails at the other end of the partial duplex (if T1=0 & T2=0, then a partial duplex can be produced with no tails at left end; if T1=0 or T2=0, then a partial duplex can be produce with one tail at the left end; if T1≠T2≠0, then a partial duplex can be produced with two non-complementary tails at the left end). Each tailed partial duplex A" is comprised of a duplex of two complementary nucleic acid strands of duplex A and, at one end of the duplex, two non-complementary oligonucleotide tails T4' and T3. Depending on the choice of forwarding primer, partial duplex A" can have either zero, one or two tails at the other end of the partial duplex (see, supra). Each tailed partial duplex B' is comprised of a duplex of two complementary nucleic acid strands of duplex B and, at one end of the duplex, two non-complementary oligonucleotide tails T3' and T4. Depending on the choice of forwarding primer, partial duplex B' can have either zero/one/two tails at the other end of the partial duplex (see, supra). Each tailed partial duplex B" is comprised of a duplex of two complementary nucleic acid strands of duplex B and, at one end of the duplex, two non-complementary oligonucleotides T4' and T3. Depending on the choice of forwarding primer, partial duplex B" can have either zero, one or two tails at the other end of the partial duplex (see, supra).

In a preferred embodiment of the invention, the nucleic acids can be prepared to detect a single base mutation between the target nucleic acid and the reference nucleic acid according to the methods described in co-pending U.S. application Ser. No. 10/071,302, the content of which is hereby incorporated by reference in its entirety. Briefly, in order to increase the sensitivity of the present detection method for a single base difference between short (<100 bp) target and reference nucleic acids, an additional mutation can be introduced either 5' or 3' to the site of the potential difference in either the target nucleic acid or in the reference nucleic acid. The additional mutation can be introduced, for instance, by using a forward primer that hybridizes to a sequence 5' of the potential single base difference and is capable of introducing such a mutation. Or alternatively, the additional mutations can be introduced by using a reverse primer that hybridizes to a sequence 3' of the potential single base difference and is capable of introducing such a mutation. Other methods of introducing such mutations will be apparent to those of skill in the art. For instance, the mutation can be introduced in two synthetic oligos that correspond to each of the two strands of reference partial duplexes and therefore can be used to make the desired reference partial duplexes with predefined mutations.

In certain embodiments, target or reference partial duplexes can be prepared by hybridization of one strand of a PCR amplicon with a synthetic oligonucleotide that is partially complementary to the PCR amplicon. FIG. 2 illustrates the preparation of a partial duplex A' using this method. Amplicon A can be prepared by PCR using forward primer F and reverse primer R. The polymorphism of interest (SNP) should be located between F and R so that it is amplified from the template DNA. Primer F or R or both can be completely complementary to the template DNA (T1=0 or T2=0 or T1 & T2=0). Alternatively, primers F and R can have, in addition to 3' portions (f and r, respectively) that are complementary to the template DNA, 5' portions (T1 and T2, respectively) that are not complementary to the template DNA. While T1 and T2 are not complementary to each other, T1 can be complementary to T1' and T2 can be complementary to T2'.

Amplicon A can then be contacted with synthetic oligonucleotide O that is partially complementary to one strand of amplicon A. O can be composed of a middle part M, and a left portion T3 or a right portion T4, or both T3 and T4. M can be fully or partially complementary to a portion of amplicon A so that O and A can hybridize to form partial duplex A'. After denaturing/re-annealing, a partial duplex A' can form through hybridization of O and the portion of amplicon A that is fully or partially complementary to O. The site of the polymorphism of interest should be within a sequence that corresponds to M. At least one end of O (T3 or T4, or both T3 and T4) should not be complementary to amplicon A. When only one end (T3 or T4) is not complementary to amplicon A, one tailed region can form at one end of the partial duplex. When both ends (T3 & T4) are not complementary to amplicon A, two tailed region can form, one at each end. Although it is shown in FIG. 2 that part of f and r are included in M, it is possible that M does not contain any sequence of f or r. Alternatively, the whole sequence of f and/or r, their complements, or portions thereof can be included in M.

In certain embodiments of the invention, a reference partial duplex can be formed by the hybridization of two synthetic oligonucleotides that correspond to the target sequence. The reference partial duplex is described in detail above. One or both strands of the reference partial duplex can be prepared by synthetic methods known to those of skill in the art. The strands of the reference partial duplex can then be contacted with each other under conditions wherein they are capable of hybridizing to form a reference partial duplex.

This example and other methods of preparing partial duplexes should be apparent to the skilled artisan and fall within the scope of the instant invention.

5.3.3 Formation of a Four-Way Structure

In order to detect a difference between sequences A and B, partial duplexes (A', A", B', B") comprising sequences A and B are brought into contact under conditions where the complementary tails are capable of annealing to one another, thereby initiating the formation of a four-way complex, as depicted in FIG. 1. Typical four-way complexes include Holliday junctions as are known to those of skill in the art. The resulting complexes C1, C2, C3, C4 are subjected to conditions where branch migration can occur. Branch migration is restricted from proceeding in the direction of the tails, because the tails on a given partial duplex are not complementary to one another, e.g., T1 is not complementary to T2'. However, branch migration can occur in the other direction to the extent that the reference and target sequences are the same. If the two sequences are identical, branch migration can proceed to the ends of the strands, resulting in the dissociation of the complex into two duplexes, each comprising one strand from each of the original partial duplexes. On the other hand, if the target and reference sequences are different, branch migration past this point of difference can result in a mismatch in the newly formed duplex. Under the conditions used in the practice of the instant invention, the presence of such a difference will actually block branch migration, resulting in a stabilized four-way complex. As a result, the presence of a difference between the two sequences can be manifested in the creation of a stabilized four-way complex that, in the absence of the difference, would resolve into two duplexes.

It will be apparent to the skilled artisan that the right terminus of the tailed partial duplex A' has, as the end part of each strand, sequence T4 and T3', respectively, that are complementary to T4' and T3, respectively, that are tails at the right terminus of B" and are not complementary to each other. When four-tailed partial duplexes A', A", B', B" are present in the same solution under the appropriate conditions, two four-way complexes (complex C1 and C2) comprising partial duplex A' and B" can form. One can form as the result of the hybridization of tail T1 of A' with tail T1' of B" and hybridization of tail T2' of A' with tail T2 of B". Another can form as a result of the hybridization of tail T3' of A' with tail T3 of B" and the hybridization of tail T4 of A' with tail T4' of B". In addition, two more four-way complexes C3 and C4 can form from partial duplexes A" and B'. One can form when tail T1' of A" hybridizes with tail T1 of B' and when tail T2 of A" hybridizes with tail T2' of B'. The other can form when tail T3 of A" hybridizes with tail T3' of B' and when tail T4' of A" hybridizes with T4 of B'.

In addition, four tailed partial duplexes A', A", B' and B" can form concatemers. For instance, three partial duplexes B", A' and a second partial duplex B" can form a concatamer with two four-way complexes junctions. However, concatemers B"-A'-B" do not prevent the detection of differences between sequence A and sequence B. If sequences A and B are identical, then migration of both four-way complexes in the B"-A'-B" should go to completion resulting in resolution of the entire concatemer into three duplexes. If there is a difference between sequences A and B, then both four-way complexes within the concatamer will be stabilized. Detection of the stabilized four-way complexes can indicate the difference between sequences A and B.

The skilled artisan using the teaching provided herein and knowledge generally available to the skilled artisan can determine appropriate conditions for hybridization of the tails and the resulting formation of a four-way complex of any specific duplexes. See, for example, Sambrook et al., *Molecular Cloning, A Laboratory Manual*, second edition, Cold Spring Harbor Laboratory (1989), Panyutin and Hsieh, 1993, supra, and U.S. Pat. No. 6,013,439.

The four-way complexes C1, C2, C3 and C4 are subject to branch migration conditions wherein, because tails T1 and T2 and tails T3 and T4 are different, the branch migration can only proceed away from the tails whose hybridization initiates four-way complex formation. If there is no mismatch between A and B, the branch migration of complex C1, C2, C3 and C4 can proceed away from the tail all the way to the other end of the partial duplexes. As a result, each of the four complexes C1, C2, C3 and C4 resolve into duplexes (FIG. 1A). Alternatively, if there is a mismatch or mismatches between A and B, the branch migration of complex C1, C2, C3 and C4 proceeding in the direction away from the tail is halted by the mismatch and stabilized four-way complexes C1, C2, C3 and C4 form (FIG. 1B). In one embodiment of the invention, branch migration is conducted in the presence of an ion such as $Mg^{++}$, which enhances the tendency of a mismatch to impede spontaneous DNA migration and hence stabilizes four-way complexes involving such a mismatch. A preferred concentration range for $Mg^{++}$ is 1 to 10 mM. It should be noted that stabilization can be achieved by means of other ions, particularly divalent cations such $Mn^{++}$ or $Ca^{++}$, or by a suitable combination of ions. In a particularly preferred embodiment, branch migration is achieved by incubation at 65° C. for about 20–120 minutes in buffer containing 4 mM $MgCl_2$, 50 mM KCl, 10 mM Tris-HCl, pH 8.3. A description of branch migration conditions suitable for the formation of stabilized four-way complex as a consequence of a single base mismatch can be found, for example, in Panyutin and Hsieh, 1993, supra, which is hereby incorporated by reference in its entirety.

5.3.4 Detection of Four-Way Complexes

Detection of stable four-way complexes (C1, C2, C3 or C4) can be used as to indicate the presence of a difference between nucleic acids A and B. The absence of stabilized four-way complexes, on the other hand, can be used to indicate the lack of a difference between nucleic acids A and B. According to the present invention, the stabilized four-way complex indicative of a difference between nucleic acids A and B can be detected by the methods described below. For instance, the stabilized four-way complex can be detected by contacting the nucleic acids with a detection molecule and in a solution comprising a tracer molecule. The detection molecule is a molecule that is capable of specifically binding a four-way complex. The tracer molecule can be any molecule capable of selectively binding the detection molecule. When co-existing in solution, the tracer molecule can compete with the four-way complex for binding to the detection molecule. Preferably, the tracer molecule comprises one or more oligonucleotides that are capable of forming a stable or immobile four-way complex. Significantly, the tracer molecule also comprises a detectable label. The detectable label should be capable of generating a detectable signal that is sensitive to binding of the tracer molecule by the detection molecule. In other words, the detectable signal upon binding by the detection molecule should be distinguishable from the detectable signal in the absence of binding by the detection molecule. The detectable signal can be detected by methods known to those of skill in the art for detecting the signal. In the absence of a four-way complex of the nucleic acids, the tracer molecule is capable of binding the detection molecule. If the nucleic acids are different, the stabilized four-way complex of the nucleic acids can compete or inhibit the binding of the tracer molecule with the detection molecule thereby indicating a difference between the nucleic acids.

5.3.4.1 The Tracer Molecule

The tracer molecule can be any molecule that has a detectable label and is capable of selectively binding the detection molecule. Preferably, the tracer molecule can be any nucleic acid that comprises a detectable label and a stable or immobilized four-way complex. When co-existing in solution, the tracer molecule can compete with the four-way complex for binding to the detection molecule. The tracer molecule can comprise a detectable label and one, two, three, four or more polynucleotide strands. If the tracer molecule comprises more than one polynucleotide strand, the polynucleotide strands can be linked together by any method known to those of skill in the art. For instance, they can be linked together covalently or non-covalently. Covalent linkages can be direct or via an optional linker. Preferably, the polynucleotide strands are linked together at least non-covalently via specific hybridization of corresponding base pairs as discussed below.

Typical tracer molecules are illustrated in FIG. 3. Tracer molecule 60 comprises four oligonucleotides, tracer molecule 90 comprises three oligonucleotides, tracer molecule 100 comprises two oligonucleotides and tracer molecule 110 comprises one oligonucleotide.

A tracer molecule comprises a stable or immobile four-way complex. Stable or immobile four-way complexes of oligonucleotides include those described in Shida et al., 1996, *J. Biochem.* 119:653–658 and in Pikkemaat et al., 1994, *Biochemistry* 33:14896–14907, the contents of which are hereby incorporated by reference in their entireties. For instance, tracer molecule 60 comprises a stable or immobile four way complex of four oligonucleotides 62, 64, 66 and 68. First oligonucleotide 62 comprises strand 70 which is complementary to strand 84 of fourth oligonucleotide 68. First oligonucleotide 62 also comprises strand 72 which is complementary to strand 74 of second oligonucleotide 64. Second polynucleotide 64 comprises strand 76 which is complementary to strand 78 of third oligonucleotide 66. Finally, third oligonucleotide 66 comprises strand 80 which is complementary to strand 82 of fourth oligonucleotide 68. The various complementary strands should be sufficiently complementary so that they are capable of hybridizing under the appropriate conditions. Preferably, the complementary strands are 100% complementary.

A tracer molecule comprising three oligonucleotides can be synthesized by linking any two oligonucleotides of tracer molecule 60. For instance, tracer molecule 90 can be created by linking oligonucleotides 62 and 64 of tracer molecule 60. A tracer molecule comprising two oligonucleotides can be created by linking any two oligonucleotides of tracer molecule 60. For instance, tracer molecule 100 can be created by linking oligonucleotides 62 and 64 and linking oligonucleotides 66 and 68 of tracer molecule 60. A tracer molecule comprising one oligonucleotide can be created by linking any three or four oligonucleotides of tracer molecule 60. For instance, tracer molecule 110 can be created by linking oligonucleotides 62 and 64, linking oligonucleotides 66 and 68 and by linking oligonucleotides 64 and 66 of tracer molecule 60.

Oligonucleotide strands of the tracer molecule can be linked together by any method known to those of skill in the art. For instance, they can be linked covalently, either directly or by way of an optional linker, or non-covalently. The optional linker can be any molecule used by those of skill in the art to link two other molecules. The linker may be rigid, semi-rigid or flexible, hydrophilic or hydrophobic, long or short, etc. A plethora of linkers suitable for linking molecules are known in the art. Preferred linkages are polynucleotide linkages or polynucleotide analogs or mimics. Preferably, the 3' terminus of a first oligonucleotide is linked to the 5' terminus of a second polynucleotide.

Of course, in certain embodiments, the oligonucleotides of the invention can be prepared synthetically by techniques known to those of skill in the art. Where the optional linkers are polynucleotides, oligonucleotides, nucleotides or other moieties amenable to synthetic techniques, the entire tracer molecule can be prepared by standard synthetic techniques, for example, by automated synthesis. Alternatively, portions of the tracer molecule can be made synthetically and combined under conditions where the portions are capable of hybridizing to form a tracer molecule. Optional linkers can be added where convenient during preparation according to principles known to those of skill in the art.

The tracer molecule also comprises a detectable label 86. The detectable label can be any label that is capable of generating a signal that can be detected by methods known to those of skill in the art. Preferably, the signal can be sensitive to the binding of the tracer molecule by the detection molecule. In particular, the signal from a tracer molecule bound by a detection molecule should be distinguishable from the signal from an unbound tracer molecule.

The detectable label can be linked to any portion of the tracer molecule known to those of skill in the art to be suitable for such a linkage. For instance, the label can be linked to the backbone of the tracer molecule or to a nucleobase of the tracer molecule. Preferably, the detectable label can be linked to the tracer molecule at or near the site of the four-way junction. In certain embodiments, the label is linked to a nucleotide position 5, 4, 3, 2 nucleotides away from the site of the four-way junction. In certain embodiments, the label is linked to a nucleotide adjacent to the four-way junction or to a nucleotide within the four-way junction.

While not intending to be bound by any particular theory of operation, the signal from the detectable label can be a signal that is sensitive to the rate of rotation of the tracer molecule. In certain embodiments of the invention, the tracer molecule rotates at a slow rate when bound by a detection molecule or molecules and at a rapid rate when not bound by a detection molecule. Measurement of the signal can thus indicate the binding state of the tracer molecule. For example, suitable detectable labels emit a first signal when the tracer molecule is rotating rapidly and a second signal when the tracer molecule is rotating slowly. Measurement of the first signal indicates that the tracer molecule is unbound while measurement of the second signal indicates that the tracer molecule is bound by the detection molecule. Suitable techniques for measuring the rotation rate of the tracer molecule include, but are not limited to, fluorescence polarization.

Suitable detectable labels include, but are not limited to, fluorescent moieties and metal-ligand charge transfer complexes. Suitable fluorescent moieties include, for example, fluorescein, rhodamine, cy dyes, BODIPY, and other fluorescent moieties known to those of skill in the art. Suitable metal-ligand charge transfer complexes include Ru, Os, Re and other metal-ligand charge transfer complexes known to those of skill in the art.

The detectable label 86 can be linked to an oligonucleotide of the tracer molecule by any method known to those of skill in the art. For instance, detectable label 86 and an oligonucleotide can be linked covalently, either directly or by way of an optional linker, or non-covalently. The optional linker can be any molecule used by those of skill in the art to link two other molecules. Any of the linkers described above can be used to link detectable label 86 to an oligonucleotide tracer molecule.

5.3.4.2 Contact with the Detection Molecule

To detect the four-way complex of the test polynucleotide and reference polynucleotide, the polynucleotides can be contacted with a detection molecule in a solution comprising a tracer molecule as described above.

The detection molecule can be any molecule or molecules known to those of skill in the art to specifically bind four-way structures such as Holliday structures. In a preferred embodiment, a protein is used to detect a stabilized four-way structure. Many proteins from various organisms have been shown specifically bind four-way structures. Those proteins include but are not limited to: RuvA, RuvC, RuvB, RusA, RuvG of *E. coli* and proteins/mutants derived from RuvA, RuvC, RuvB, RusA, RuvG. In addition, such proteins include homologs (such as functional homologs) of RuvA, RuvC, RuvB, RusA, RuvG from various other organisms, such as homologs of RuvA, RuvC, RuvB, RusA, and RuvG derived from mammals, Cce1 and spCce1 from yeast, Hjc from *Pyrococcus furiosusa*, and various other resolvases and recombinases that can specifically bind to four-way complexes.

In particularly convenient embodiments of the invention, thermostable proteins are used to detect the presence of a four-way complex. Such thermostable proteins include thermostable homologs of RuvA, RuvC, RuvB, RusA, and RuvG that are derived from thermophilic organisms— organisms selected from the group consisting of *Thermus aquaticus*, *Thermus flavus*, *Thermus thermophilus* and other thermophilic organisms known to those of skill in the art. Hjc from *Pyrococcus furiosusa* is one example of an appropriate thermostable protein with specificity for four-way complex.

The preparation and properties of a number of such proteins useful in the practice of the present invention have been described, for example, in the following list of literature references, all of which are incorporated herein in their entirety: Davies and West, supra; Whitby et al., supra; Iwasaki et al., 1992, *Genes Dev.* 6:2214–2220; Parsons et al., 1992, *Proc. Natl. Acad. USA* 89:5452–5456; Traneva et al., 1992, *Mol. Gen. Genet.* 235:1–10; Rafferty et al., 1996, *Science* 274:415–421; Hargreaves et al., 1999, *Acta Crystallogr. D. Biol. Crystallogr.* 55(Pt 1):263–265; Hargreaves et al., 1998, *Nature Struct Biol.* 5(6):441–446; Dunderdale et al., 1994, *J. Biol. Chem.* 267(7):5187–5194; Ariyoshi et al., 1994, *Cell* 78(6):1063–1072; Sharples et al., 1994, *EMBO* 13(24):6133–6142; Rice et al., 1995, *Cell* 82(2):209–220; Bujacz et al. 1995, *J. Mol. Biol.* 253(2):333–346; Rice et al., 1996, *Curr. Opin. Struct. Biol.* 6(1):76–83; Suck, 1997, *Biopolymer* 44(4):405–421; White et al., 1997, *J. Mol. Biol.* 266(1):122–134; Whitby et al., 1997, *J. Mol. Biol.* 271(4): 509–522; Bidnenko et al., 1998, *Mol. Microbiol.* 28(4): 823–834; Raaijmakers et al., 1999, *EMBO* 18(6): 1447–1458; Komori et al., 1999, *Proc. Natl. Acad. Sci. USA* 96(16):8873–8878; Komori et al., 2000, *J. Biol. Chem.* 275:40385–40391; Sharples et al., 1999, *J. Bacteriol.* 181 (8):5543–5550; Sharples et al., 1993, *Nucleic Acid Research* 21(15):3359–3364.

In preferred embodiments, the detection molecule is RuvA. In other preferred embodiments, the detection molecule is RuvC mutant that lacks the wild-type form of the enzyme's Holliday junction-specific endonuclease activity but retains the ability to specifically bind four-way complexes. Such mutants include D7N, E66Q, D138N, D141N, D7N, E66D, D138E, and ruvC51, and others described, for example, in Saito et al., 1995, *Proc. Natl. Acad. Sci. USA* 92:7470–7474 and in Sharples et al., 1993, *Nucleic Acid Research* 21:3359–3364, the contents of which are hereby incorporated by reference in their entireties.

The detection molecule is contacted with the nucleic acids under conditions in which the detection molecule is capable of selectively binding the tracer molecule or a four-way complex comprising the target polynucleotide and reference polynucleotide. Such conditions depend on the identity of the detection molecule and are within the knowledge of those of skill in the art. Preferably, the conditions are chosen so that the detectable label of the tracer molecule can be detected to identify the binding state of the tracer molecule.

5.3.4.3 Detection of a Difference between the Nucleic Acids

Any difference between the nucleic acids can be detected by detecting the binding of the tracer molecule with the detection molecule with an appropriate detection method under the appropriate conditions. The conditions of detection depend upon the identity of the detection molecule and will be apparent to those of skill in the art. The conditions should be chosen so that the binding of the detection molecule is sensitive to the amount of four-way complexes of the nucleic acids present in the solution. In particular, the amount of the tracer molecule and the amount of the detection molecule should be chosen so that a sufficient amount of the detection molecule can bind a stable four-way complex of the nucleic acids to detectably alter the binding of the detection molecule to the tracer molecule. Under such conditions, a change in the binding of the tracer molecule with the detection molecule indicates a difference between the nucleic acids.

The binding of the tracer molecule with the detection molecule can be detected by, for instance, measuring the rotation rate of the tracer molecule. While not intending to be bound by any particular theory of operation, if the tracer molecule is free of the detection molecule, the tracer molecule should be capable of rotating at a more rapid rate than the rate of rotation of the tracer molecule bound with the detection molecule.

The rotation rate of the tracer molecule can be measured by any technique known to those of skill in the art for measuring the rotation rate of a molecule. For instance, the rotation rate of a tracer molecule comprising a suitable label can be measured by fluorescence polarization. Suitable labels include, for example, the fluorescent labels discussed above. Fluorescence polarization is a technique well known to those of skill in the art that can be used to measure the rotation rate of a molecule (see, e.g., Perrin, 1926, *J. Phys. Radium* 7:390; Weber, 1953, *Adv. Protein Chem.* 8:415; Weber, 1956, *J. Opt. Soc. Am.* 46:962).

Fluorescence polarization (FP) is a homogeneous method for detection of molecular interactions. A fluorescent molecule can be excited by either horizontally or vertically polarized monochromatic light. The emitted light can be measured in both vertical and horizontal planes, and the polarization value of the molecule can be calculated using the formula, wherein I is intensity:

$$\text{Polarization value} = (I_{vertical} - I_{horizontal})/(I_{vertical} + I_{horizontal})$$

The polarization value of a molecule is proportional to the molecule's rotational relaxation time during the fluorophore's period of excitation. This relaxation time can be proportional to the molecular size, so that small molecules can have low polarization values and large molecules have high polarization values. The increase of molecular size of a fluorescent molecule can be brought about by its binding to another molecule.

When the rotation rate of the tracer molecule is measured to determine the binding of the detection molecule and thereby the presence of a four-way complex of the nucleic acids, the rotation rate of the tracer molecule can be compared to the rotation rate of a control molecule under the appropriate conditions. For instance, the rotation rate of the tracer molecule in the presence of the nucleic acids can be compared to the rotation rate of the tracer molecule in the absence of the nucleic acids. A significant increase in the rotation rate of the tracer molecule can indicate that a four-way complex of the nucleic acids is competing with the tracer molecule for binding by the detection molecule. Alternatively, the rotation rate of the tracer molecule in the presence of the detection molecule can be measured prior to contact with the nucleic acids. The tracer molecule can then be contacted with the nucleic acids, and the rotation rate of the tracer molecule can again be measured. A significant increase in the rotation rate of the tracer molecule can indicate the presence of a stabilized four-way complex of the nucleic acids. Other control measurements will be apparent to those of skill in the art.

The presence of a stabilized four-way complex of the nucleic acids measured by any of the techniques discussed above indicates a difference between the nucleic acids.

The invention having been described, the following examples are intended to illustrate, and not limit, this invention.

6. EXAMPLES

6.1 Example 1

Construction of Tracer Molecules

In this example, several tracer molecules were synthesized and evaluated for use in the methods of the invention. The tracer molecules of this example are useful for detecting differences between any pair of nucleic acids including pairs of nucleic acids from the Examples below.

All oligonucleotides were purchased from Operon Technologies Inc. (Alameda, Calif.).

In this example, several tracer molecules were made with nucleic acids that were synthesized and linked to fluorescent labels. The nucleic acids were capable of forming stabilized four-way complexes. These nucleic acids were examined to identify a tracer molecule/molecules that displays a low polarization value in an unbound state and a high increase in polarization value upon binding RuvA protein.

The first potential tracer molecule is the four-stranded nucleic acid $HJ_{24}$. $HJ_{24}$ comprised the following polynucleotide strands, each having 24 nucleotides:

| Strand 1: | GCCACAGCCAGTGAGCCCATTCCG | (SEQ ID NO:1) |
| Strand 2: | CGGAATGGGCTCTGACCGAGCACG | (SEQ ID NO:2) |
| Strand 3: | CGTGCTCGGTCACTCGGCAGATGC | (SEQ ID NO:3) |
| Strand 4: | GCATCTGCCGAGACTGGCTGTGGC | (SEQ ID NO:4) |

Strand 1 of $HJ_{24}$ was labeled with fluorescein (Qiagen Operon Product Guide, 2002, Operon Technologies Inc., Alameda, Calif., p. 22) at 5'-end via a phosphodiester bond.

The four-stranded nucleic acid $HJ_{18}$ (Shida et al., 1996, *J. Biochem*. 119:653–658) comprised the following polynucleotide strands, each having 18 nucleotides:

| Strand 1: | GCGCATAGTCCGAATGGC | (SEQ ID NO:5) |
| Strand 2: | GCCATTCGGTGAGCAGCG | (SEQ ID NO:6) |
| Strand 3: | CGCTGCTCAGGATTGACG | (SEQ ID NO:7) |
| Strand 4: | CGTCAATCCACTATGCGC | (SEQ ID NO:8) |

The second potential tracer molecule is $HJ_{18}$-1. The four-stranded nucleic acid $HJ_{18}$-1 comprised the same four polynucleotide strands as $HJ_{18}$. Strand 1 of $HJ_{18}$-1 comprised the same four polynucleotide strands as $HJ_{18}$ and was labeled with fluorescein (Qiagen Operon Product Guide, 2002, Operon Technologies Inc., Alameda, Calif., p. 22) at the 5'-end via a phosphodiester bond.

The third potential tracer molecule is $HJ_{18}$-2. The four-stranded nucleic acid. $HJ_{18}$-2 comprised the same four polynucleotide strands as $HJ_{18}$. In $HJ_{18}$-2, strand 1 was labeled internally with fluorescein-dT (Qiagen Operon Product Guide, 2002, Operon Technologies Inc., Alameda, Calif., p. 22; Glen Research Catalog No. 10-1056) at position 9.

The four stranded nucleic acid $HJ_{17}$ (Roe et al., 1998, Molecular Cell 2: 361–372) comprised the following polynucleotide strands, each having 17 nucleotides:

| Strand 1: | TCCTTGCTAGGACATGC | (SEQ ID NO:9) |
| Strand 2: | TGCACCATGTAGCAAGG | (SEQ ID NO:10) |
| Strand 3: | TCGGCAGATCATGGTGC | (SEQ ID NO:11) |
| Strand 4: | TGCATGTCCATCTGCCG | (SEQ ID NO:12) |

The fourth potential tracer molecule is $HJ_{17}$-1. The four-stranded nucleic acid $HJ_{17}$-1 comprised the same four polynucleotide strands as $HJ_{17}$. Strand 2 of $HJ_{17}$-1 was labeled with fluorescein (Qiagen Operon Product Guide, 2002, Operon Technologies Inc., Alameda, Calif., p. 22) at the 3'-end via a phosphodiester bond.

The fifth potential tracer molecule is $HJ_{17}$-1. The four stranded nucleic acid $HJ_{17}$-2 comprised the same four polynucleotide strands as $HJ_{17}$. Strand 2 of $HJ_{17}$-2 was labeled internally with fluorescein-dT at position 10.

The one stranded nucleic acid $HJ_{46}$ (Pikkemaat et al., 1994, *Biochemistry* 33:14896–14907) comprised a polynucleotide having 46 nucleotides of the following sequence:

GCACTGCTACGCTTGCGTCGGCTTGC-CGCCACTTGTGGAGCAGTGC  (SEQ ID NO:13)

$HJ_{46}$ is capable of folding spontaneously into a structure resembling a four-way junction, with four double-stranded arms, three of which are hairpins. The sixth potential tracer molecule is $HJ_{46}$-1. The one-stranded nucleic acid $HJ_{46}$-1 comprised the same polynucleotide strand as $HJ_{46}$ except that $HJ_{46}$-1 was labeled with fluorescein at the 5'-end. The sixth potential tacer molecule is $HJ_{46}$-2. The one-stranded nucleic acid $HJ_{46}$-2 comprised the same polynucleotide strand as $HJ_{46}$ except that $HJ_{46}$-2 was labeled internally with fluorescein-dT at position 8.

All of the seven potential tracer molecules described above have the structure of a four-way junction. To prepare the five potential tracer molecules ($HJ_{24}$, $HJ_{18}$-1, $HJ_{18}$-2, $HJ_{17}$-1 and $HJ_{17}$-2) that are comprised of four polynucleotide strands, equal amounts of the four polynucleotide strands at 12.5 mM each were mixed and 10x commercial AmpliTaq buffer (Applied Biosystems) was added to 1×. The mixtures were then heat-denatured (2 min at 94° C.) and cooled to room temperature to allow the annealing of strands and the formation of four-way junctions. To prepare the two potential tracer ($HJ_{46}$-1 and $HJ_{46}$-2) molecules that are comprised of a single polynucleotide strand, the single strand was heat-denatured (2 min at 94° C.) and then cooled to room temperature to allow the formation of a Holliday Junction-like structure.

To assay fluorescence polarization of the potential tracer molecules, each potential tracer was contacted with RuvA. For each potential tracer, 1 ml of 100 nM of the potential tracer was mixed with 3.5 ml 1×AmpliTaq buffer and then mixed with 0.5 ml 50 mM RuvA from *E. coli* (total reaction volume 5 ml in 1×AmpliTaq buffer) and incubated at room temperature for 5 min. 100 ml of 1×AmpliTaq buffer was then added, and the sample was transferred into a 6×50 mm glass tube and fluorescence polarization was measured using the Beacon 2000 Fluorescence Polarization Analyzer (PanVera Corp., Madison, Wis.). The fluorescence polarization of each nucleic acid is provided in Table 1.

TABLE 1

Fluorescence Polarization of HJ-RuvA Complexes

| Tracer | Free Tracer (in the Absence of RuvA) | FP of Tracer-RuvA Complex |
|---|---|---|
| $HJ_{24}$ | 146.6 | 169.2 |
| $HJ_{18}$-1 | 132.6 | 180.5 |
| $HJ_{18}$-2 | 63.5 | 357.0 |
| $HJ_{17}$-1 | 150.4 | 236.5 |
| $HJ_{17}$-2 | 73.1 | 250.6 |
| $HJ_{46}$-1 | 122.5 | 128.5 |
| $HJ_{46}$-2 | 59.6 | 71.9 |

As shown in Table 1, several potential tracer molecules tested in this example showed significant increases in fluorescence polarization upon binding RuvA. Overall, internally fluorescein-labeled molecules showed greater increases than comparable terminally fluorescein-labeled molecules. Two potential tracer molecules $HJ_{18}$-2 and $HJ_{17}$-2 displayed the highest polarization values when bound to RuvA. $HJ_{18}$-2, with a high bound/free fluorescence polarization ratio, was selected as the tracer molecule for the examples below.

6.2 Example 2

Preparation of Nucleic Acids

In this example and the examples that follow, compositions and methods for the detection of differences between nucleic acids using fluorescence polarization according to the present invention are demonstrated. In this example, tailed reference nucleic acid and tailed target nucleic acids were prepared for use in the methods.

Five regions of human genomic DNA that contain known single-nucleotide polymorphisms (SNPs) were PCR-amplified using tailed reverse primers to enable the formation of four-way complexes. The sequence of these regions, the location and identity of the respective SNPs within them and the sequences of the primers can be found in the National Center for Biotechnology Information (NCBI) SNP database (NCBI). The NCBI accession IDs of the SNPs used were as follows: ss4215, ss4217, ss4213, ss4141, ss4212 and ss4030.

The genomic DNA samples were obtained from the M08PDR panel (Coriell Cell Repository, Camden, N.J.). Two genomic DNA samples were amplified for each SNP. For each SNP, one sample was a homozygote and the other was a heterozygote. The genotypes of these samples were determined previously (Lishanski, 2000, *Clinical Chemistry* 46:1464–1470).

The primer sequences for amplifying genomic DNA are listed in Table 2.

TABLE 2

Primers for Amplification of Nucleic Acids

| SNP | Primer | | Sequence |
|---|---|---|---|
| 4215 | F | (SEQ ID NO:14) | CTGTGTTATTTGCTGATCCTG |
| | Rt1 | (SEQ ID NO:15) | ACCATGCTCGAGATTACGAGGTAAACTTTCTGAGCCTCTGG |
| | Rt2 | (SEQ ID NO:16) | GATCCTAGGCCTCACGTATTGTAAACTTTCTGAGCCTCTGG |
| 4217 | F | (SEQ ID NO:17) | CATTAGCTTAAAAGCTGTCTTTTGC |
| | Rt1 | (SEQ ID NO:18) | ACCATGCTCGAGATTACGAGGGTTTGCTGGAAGAAAGCAG |
| | Rt2 | (SEQ ID NO:19) | GATCCTAGGCCTCACGTATTGGTTTGCTGGAAGAAAGCAG |
| 4213 | F | (SEQ ID NO:20) | AAAACCCTGTTGATATTGGCC |
| | Rt1 | (SEQ ID NO:21) | ACCATGCTCGAGATTACGAGCTGAATACTCTCCATCCTTGCC |
| | Rt2 | (SEQ ID NO:22) | GATCCTAGGCCTCACGTATTCTGAATACTCTCCATCCTTGCC |
| 4141 | F | (SEQ ID NO:23) | ACCACATCCTCTCATTCGTTG |
| | Rt1 | (SEQ ID NO:24) | ACCATGCTCGAGATTACGAGGGGGTCTCTGCAGTTAACCA |
| | Rt2 | (SEQ ID NO:25) | GATCCTAGGCCTCACGTATTGGGGTCTCTGCAGTTAACCA |
| 4212 | F | (SEQ ID NO:26) | TGATGTCAAAATAGCTCCATGC |
| | Rt1 | (SEQ ID NO:27) | ACCATGCTCGAGATTACGAGAATATGCAAAGTAATTTTCTGGCC |
| | Rt2 | (SEQ ID NO:28) | GATCCTAGGCCTCACGTATTAATATGCAAAGTAATTTTCTGGCC |
| 4030 | F | (SEQ ID NO:29) | TTAATGCAGTACATGTCCTTTTGG |
| | Rt1 | (SEQ ID NO:30) | ACCATGCTCGAGATTACGAGCAAGAGTTCTTGGGGGCATA |
| | Rt2 | (SEQ ID NO:31) | GATCCTAGGCCTCACGTATTCAAGAGTTCTGGGGGCATA |

TABLE 2-continued

Primers for Amplification of Nucleic Acids

| SNP | Primer | Sequence |
|---|---|---|
| 5bp del | F (SEQ ID NO:32) | TCAAATTGTTGGCTAACACCA |
| | Rt1 (SEQ ID NO:33) | ACCATGCTCGAGATTACGAGTACTGGTGTACCGTCCATGT |
| | Rt2 (SEQ ID NO:34) | GATCCTAGGCCTCACGTATTTACTGGTGTACCGTCCATGT |

In Table 2, for each SNP F is a forward PCR primer, and R is a reverse PCR primer. In the reverse primers, t1 and t2 are the "tail" sequences (underlined) that are common for all 5 amplicons. The F and R primer sequences can be found in NCBI assay ID ss4215, ss4217, ss4213, ss4141 and ss4212.

PCR amplifications were carried out using a PTC-200 DNA Engine thermocycler (MJ Research Inc., Waltham, Mass.). 35 PCR cycles were performed with 10 s denaturation at 94° C., 15 s reannealing at 62° C. and 45 s extension at 72° C. The cycling was preceded by a 10-min incubation at 95° C. to activate AmpliTaq Gold™ DNA polymerase (Applied Biosystems, Foster City, Calif.) and followed by 2 min of denaturation at 95° C. and 30-min incubation at 65° C. (reannealing and branch migration). The reaction mixtures (100 ml) contained 100 ng genomic DNA, 2.5 U AmpliTaq Gold™ DNA polymerase, 200 mM each dNTP and 250 nM each primer in BMB buffer (10 mM Tris-HCl, pH 8.3, 50 mM KCl, 4 mM $MgCl_2$ and 200 mg/ml BSA).

6.3 Example 3

Genotyping by Fluorescence Polarizatation

In this example, the genotypes of eight genomic DNA samples of Example 2 were determined by fluorescence polarization measurements with RuvA and the tracer molecule $HJ_{18}$-2 of Example 2. The eight genomic DNA samples were amplified using primers specific for SNP 4215 as described in Example 1.

20 ml PCR product was subjected to branch migration in BMB buffer. To this sample, was added 80 ml 250 pM tracer molecule $HJ_{18}$-2 in BMB buffer and 2 ml 500 nM RuvA in BMB buffer.

After 10 min incubation at room temperature the mixture was analyzed using the Beacon 2000 Fluorescence Polarization Analyzer as described above. Table 3 provides the results of the assays.

higher than that in the samples with identical nucleic acid sequences ("homozygotes").

6.4 Example 4

Preparation of Nucleic Acids with Dilution of Genomic DNA

To eliminate any possible effect of genomic DNA, several amplification products of Example 2 were subject to a second round of PCR.

An amplification product of Example 2 (after 35 amplification cycles) was diluted 1:1000 in $H_2O$. 2 ml of this dilution was further amplified using the same primers (50 ml, 20 amplification cycles). The final amplification products contained only negligible amounts of original genomic DNA.

6.5 Example 5

Fluorescence Polarization Analysis of the Genotypes of the Nucleic Acids of Example 4

In this example, the genotypes of the nucleic acids of Example 3 were determined by fluorescence polarization with the tracer molecule $HJ_{18}$-2. Samples 1–8 were prepared with the primers for SNP 4215, and samples 9–16 were prepared with the primers for SNP 4216.

20 ml PCR product was subjected to branch migration in BMB buffer. To this sample, was added 80 ml 250 pM tracer molecule $HJ_{18}$-2 in BMB buffer and 2 ml 500 nM RuvA in BMB buffer.

After 10 min incubation at room temperature the mixture was analyzed using the Beacon 2000 Fluorescence Polarization Analyzer as described above. Table 4 provides the results of the assays.

TABLE 3

FP Genotype Assay of Samples 1–8

| Sample | Genotype | Fluorescence Polarization (mp) |
|---|---|---|
| 1 | Heterozygote | 118.3 |
| 2 | Homozygote | 200.7 |
| 3 | Heterozygote | 109.3 |
| 4 | Homozygote | 206.5 |
| 5 | Heterozygote | 127.4 |
| 6 | Heterozygote | 146.5 |
| 7 | Homozygote | 197.5 |
| 8 | Heterozygote | 121.8 |

As shown in Table 3, a stabilized four-way complexes in the genomic sample competes with the tracer molecule for RuvA protein binding. As such, the fluorescence polarization values of the tracer molecules in the samples with mismatched nucleic acids ("heterozygotes") was significantly

TABLE 4

FP Genotype Assay of Samples 1–16

| Sample | Genotype | Fluorescence Polarization (mp) |
|---|---|---|
| no DNA | | 368.7 |
| 1 | Heterozygote | 156.9 |
| 2 | Homozygote | 280.9 |
| 3 | Heterozygote | 154.6 |
| 4 | Homozygote | 281.7 |
| 5 | Heterozygote | 152.2 |
| 6 | Heterozygote | 151.9 |
| 7 | Homozygote | 293.8 |
| 8 | Heterozygote | 158.9 |
| 9 | Homozygote | 212.6 |
| 10 | Heterozygote | 147.3 |
| 11 | Homozygote | 208.3 |
| 12 | Homozygote | 217.6 |
| 13 | Homozygote | 224.9 |
| 14 | Homozygote | 218.6 |

TABLE 4-continued

FP Genotype Assay of Samples 1–16

| Sample | Genotype | Fluorescence Polarization (mp) |
|---|---|---|
| 15 | Homozygote | 214.2 |
| 16 | Homozygote | 216.4 |

As shown in Table 4, a stabilized four-way complexes in the PCR products, even after dilution of genomic DNA, competes with the tracer molecule for RuvA protein binding. As such, the fluorescence polarization values of the tracer molecules in the heterozygous samples were significantly higher than those in the homozygous samples.

6.6 Example 6

Fluorescence Polarization Analysis of the Genotypes of Further Nucleic Acids of Example 4

In this Example, further assays for the genotypes of the nucleic acids of Example 4 were demonstrated. The genotypes were determined by fluorescence polarization with the tracer molecule $HJ_{18}$-2. Samples 17 and 18 were prepared with the primers for SNP 3989. Samples 19 and 20 were prepared with the primers for SNP 4141. Samples 21 and 22 were prepared with the primers for SNP 4213. Samples 23 and 24 were prepared with the primers for SNP 4030. Samples 25 and 26 were prepared with the primers for the 5 bp deletion of Example 2.

20 ml PCR product was subjected to branch migration in BMB buffer. To this sample, was added 80 ml 250 pM tracer molecule $HJ_{18}$-2 in BMB buffer and 2 ml 500 nM RuvA in BMB buffer.

After 20 min incubation at room temperature the mixture was analyzed using the Beacon 2000 Fluorescence Polarization Analyzer as described above. Table 5 provides the results of the assays.

TABLE 5

FP Genotype Assay of Samples 17–26

| Sample | Genotype | Fluorescence Polarization (mp) |
|---|---|---|
| 17 | Homozygote | 290.6 |
| 18 | Heterozygote | 212.2 |
| 19 | Homozygote | 300.2 |
| 20 | Heterozygote | 221.2 |
| 21 | Homozygote | 286.9 |
| 22 | Heterozygote | 203.1 |
| 23 | Homozygote | 311.0 |
| 24 | Heterozygote | 248.4 |
| 25 | Homozygote | 338.3 |
| 26 | Heterozygote | 207.7 |

As shown in Table 5, a stabilized four-way complex in the PCR products, competes with the tracer molecule for RuvA protein binding. As such, the fluorescence polarization values of the tracer molecules in the heterozygous samples were significantly higher than those in the homozygous samples.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entireties.

---

What is claimed is:

1. A method for detecting a difference in the sequence of two nucleic acid molecules comprising:
   a) Contacting the two nucleic acids under conditions that allow the formation of a four-way complex and branch migration;
   b) Contacting the four-way complex with a tracer molecule and a detection molecule under conditions in which the detection molecule is capable of binding the tracer molecule or the four-way complex; and
   c) Determining binding of tracer molecule to the detection molecule before and after exposure to the four-way complex, wherein competition of the four-way complex with the tracer molecule for binding to the detection molecule results in reduced binding of the tracer molecule to the detection molecule after the exposure to the four-way complex, which indicates the presence of a difference between the two nucleic acids.

2. A method for detecting a difference in the sequence of two nucleic acid molecules comprising:
   a) Contacting the two nucleic acids under conditions that allow the formation of a four-way complex and branch migration;
   b) Contacting the four-way complex with a tracer molecule and a detection molecule under conditions in which the detection molecule is capable of binding the tracer molecule or the four-way complex; and
   c) Comparing binding of the tracer molecule to the detection molecule in step b) with binding of the tracer molecule to the detection molecule in a test sample without the four-way complex, wherein reduced binding of the tracer molecule to the detection molecule in the presence of the four-way complex indicates a difference between the two nucleic acids.

3. The method of claim 1 or 2, wherein steps a) and b) are carried out simultaneously.

4. The method of claim 1 or 2, wherein under said branch migration conditions the four-way complex is capable of resolution if the nucleic acids are identical in sequence.

5. The method of claim 1 or 2, wherein under said branch migration conditions the four-way complex is not capable of resolution if the nucleic acids are not identical in sequence.

6. The method of claim 1 or 2, wherein under said branch migration conditions if a difference between the two related nucleic acid sequences is present, branch migration in the four-way complex ceases and the four-way complex is stabilized, and if no difference between the two related nucleic acid sequences is present, branch migration in the four-way complex continues until complete strand exchange occurs and the four-way complex resolves into two duplex nucleic acids, thereby forming a stabilized four-way complex.

7. The method of claim 1 or 2, wherein the difference is a mutation, an insertion, a deletion or a single base substitution.

8. The method of claim 1 or 2, wherein one of the nucleic acids is DNA.

9. The method of claim 1 or 2, wherein the four-way complex comprises a Holliday junction.

10. The method of claim 1 or 2, wherein the detection molecule is capable of selectively binding a four-way nucleic acid complex.

11. The method of claim 10, wherein the detection molecule is capable of selectively binding a Holliday junction.

12. The method of claim 11 wherein the detection molecule is selected from the group consisting of RuvA, RuvC, RuvB, RusA, RuvG, Ccel, spCcel, Hjc and mutants or analogs thereof.

13. The method of claim 11, wherein the detection molecule is thermostable.

14. The method of claim 1 or 2, wherein the tracer molecule is a nucleic acid comprising a stable four-way complex.

15. The method of claim 14, wherein the tracer molecule comprises one, two, three or four oligonucleotides.

16. The method of claim 1 or 2, wherein the tracer molecule is a nucleic acid comprising an immobile four-way complex.

17. The method of claim 1 or 2, wherein the tracer molecule is capable of selectively binding the detection molecule.

18. The method of claim 1 or 2, wherein the tracer molecule comprises a detectable label.

19. The method of claim 18, wherein the detectable label is capable of generating a signal upon binding of the tracer molecule to the detection molecule.

20. The method of claim 18, wherein the detectable label is a fluorescent label.

21. The method of claim 20, wherein the fluorescent label is selected from the group consisting of fluorescein, rhodamine, cyanine dyes or BODIPY.

* * * * *

SEQUENCE LISTING

<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Polynucleo#
      tide strand comprising
      HJ24 tracer molecule

<400> SEQUENCE: 1
gccacagcca gtgagcccat tccg                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Polynucleo#
      tide strand comprising
      HJ24 tracer molecule

<400> SEQUENCE: 2
cggaatgggc tctgaccgag cacg                                           24

<210> SEQ ID NO 3

```
-continued

<211> LENGTH: 24
<212> TYPE: DNA
<213> ORGANISM: Artificial Sequence
<220> FEATURE:
<223> OTHER INFORMATION: Description of Artificial Sequence: Polynucleo#
      tide strand comprising
      HJ24 tracer molecule

<400> SEQUENCE: 3
cgtgctcggt cactcggcag atgc                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Polynucleo#
      tide strand comprising
      HJ24 tracer molecule

<400> SEQUENCE: 4
gcatctgccg agactggctg tggc                                            24

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Polynucleo#
      tide strand comprising
      HJ18 tracer molecule

<400> SEQUENCE: 5
gcgcatagtc cgaatggc                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Polynucleo#
      tide strand comprising
      HJ18 tracer molecule

<400> SEQUENCE: 6
gccattcggt gagcagcg                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Polynucleo#
      tide strand comprising
      HJ18 tracer molecule

<400> SEQUENCE: 7
cgctgctcag gattgacg                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Polynucleo#
      tide strand comprising
      HJ18 tracer molecule

<400> SEQUENCE: 8
```

```
cgtcaatcca ctatgcgc                                                 18

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Polynucleo#
      tide strand comprising
      HJ17 tracer molecule

<400> SEQUENCE: 9
tccttgctag gacatgc                                                  17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Polynucleo#
      tide strand comprising
      HJ17 tracer molecule

<400> SEQUENCE: 10
tgcaccatgt agcaagg                                                  17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Polynucleo#
      tide strand comprising
      HJ17 tracer molecule

<400> SEQUENCE: 11
tcggcagatc atggtgc                                                  17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Polynucleo#
      tide strand comprising
      HJ17 tracer molecule

<400> SEQUENCE: 12
tgcatgtcca tctgccg                                                  17

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Polynucleo#
      tide strand comprising
      HJ46 tracer molecule

<400> SEQUENCE: 13
gcactgctac gcttgcgtcg gcttgccgcc acttgtggag cagtgc                  46

<210> SEQ ID NO 14
<211> LENGTH: 21
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 14
ctgtgttatt tgctgatcct g                              21

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 15
accatgctcg agattacgag gtaaactttc tgagcctctg g         41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 16
gatcctaggc ctcacgtatt gtaaactttc tgagcctctg g         41

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cattagctta aaagctgtct tttgc                          25

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 18
accatgctcg agattacgag ggtttgctgg aagaaagcag          40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 19
gatcctaggc ctcacgtatt ggtttgctgg aagaaagcag          40

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
aaaaccctgt tgatattggc c                              21

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 21
accatgctcg agattacgag ctgaatactc tccatccttg cc                    42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 22
gatcctaggc ctcacgtatt ctgaatactc tccatccttg cc                    42

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
accacatcct ctcattcgtt g                                           21

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 24
accatgctcg agattacgag ggggtctctg cagttaacca                       40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 25
gatcctaggc ctcacgtatt ggggtctctg cagttaacca                       40

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
tgatgtcaaa atagctccat gc                                          22

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Primer

```
<400> SEQUENCE: 27
accatgctcg agattacgag aatatgcaaa gtaattttct ggcc            44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 28
gatcctaggc ctcacgtatt aatatgcaaa gtaattttct ggcc            44

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 29
ttaatgcagt acatgtcctt ttgg                                  24

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 30
accatgctcg agattacgag caagagttct tgggggcata                 40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 31
gatcctaggc ctcacgtatt caagagttct tgggggcata                 40

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 32
tcaaattgtt ggctaacacc a                                     21

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 33
accatgctcg agattacgag tactggtgta ccgtccatgt                 40

<210> SEQ ID NO 34
<211> LENGTH: 40
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 34
gatcctaggc ctcacgtatt tactggtgta ccgtccatgt                    40
```